US008580063B2

(12) United States Patent
Koori

(10) Patent No.: US 8,580,063 B2
(45) Date of Patent: *Nov. 12, 2013

(54) METHOD FOR PRODUCING ENDOSCOPE FLEXIBLE TUBE

(75) Inventor: Junichi Koori, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 72 days.
This patent is subject to a terminal disclaimer.

(21) Appl. No.: 13/013,696

(22) Filed: Jan. 25, 2011

(65) Prior Publication Data

US 2011/0220270 A1    Sep. 15, 2011

(30) Foreign Application Priority Data

Mar. 15, 2010   (JP) ................... 2010-057868

(51) Int. Cl.
*B29C 47/00*   (2006.01)
*B29C 47/06*   (2006.01)
*B65H 81/00*   (2006.01)

(52) U.S. Cl.
USPC ...... 156/244.13; 156/148; 156/149; 156/169; 156/184; 156/195; 156/244.11; 156/244.12

(58) Field of Classification Search
USPC ......... 156/169, 171, 172, 173, 184, 185, 187, 156/188, 195, 244.11, 244.12, 244.13
See application file for complete search history.

(56) References Cited

U.S. PATENT DOCUMENTS 6,599,239 B2   7/2003  Hayakawa et al.
6,860,849 B2 *  3/2005  Matsushita et al. ........... 600/140

(Continued)

FOREIGN PATENT DOCUMENTS

DE    EP 0 336 806 A2    10/1989
JP    55-112505    8/1980

(Continued)

OTHER PUBLICATIONS

US Office Action for co-pending U.S. Appl. No. 13/121,538 dated Jan. 2, 2013.

(Continued)

*Primary Examiner* — Katarzyna Wyrozebski Lee
*Assistant Examiner* — Carson Gross
(74) *Attorney, Agent, or Firm* — McGinn Intellectual Property Law Group, PLLC

(57)   ABSTRACT

A method for producing an endoscope flexible tube comprising the steps of:
preparing a flexible tube assembly including a spiral tube formed by spirally winding a metal strip and a cylindrical mesh sleeve, covering the spiral tube, formed by knitting metal wires;
covering the flexible tube assembly with an outer coat from one end toward the other end of the flexible tube assembly by using an extrusion molding machine wherein the outer coat has a lower layer formed of a thermoplastic polyurethane elastomer and an upper layer formed of a thermoplastic polyester elastomer and the total thickness of the upper layer and the lower layer is made constant; and
annealing the covered flexible tube assembly at a temperature in the vicinity of the softening point of the layer lower in softening point of the upper layer and the lower layer after the step of covering the flexible tube assembly with the outer coat,
wherein in the step of covering with the outer coat, the melt viscosity ratio (thermoplastic polyurethane elastomer/ thermoplastic polyester elastomer; with reference to the exit temperature of the extrusion molding machine) between the thermoplastic polyurethane elastomer and the thermoplastic polyester elastomer is set to fall within a range from 1 to 35, and the thickness ratio between the upper layer and the lower layer is gradually varied in such a way that one of the upper layer and the lower layer has the maximum thickness at the one end and the one of the upper layer and the lower layer has the minimum thickness at the other end.

10 Claims, 7 Drawing Sheets

(56) References Cited

U.S. PATENT DOCUMENTS

| | | | |
|---|---|---|---|
| 6,916,285 B2 * | 7/2005 | Takase | 600/133 |
| 7,169,105 B2 | 1/2007 | Iwasaka et al. | |
| 7,985,315 B2 | 7/2011 | Fujii et al. | |
| 2011/0212262 A1 * | 9/2011 | Miyasaka et al. | 427/258 |

FOREIGN PATENT DOCUMENTS

| | | | |
|---|---|---|---|
| JP | 2001-161632 A | | 6/2001 |
| JP | 2001-161633 A | | 6/2001 |
| JP | 2001-333883 A | | 12/2001 |
| JP | 2002-58637 A | | 2/2002 |
| JP | 2006-281 A | | 1/2006 |
| WO | WO 2010/038738 | * | 4/2010 |

OTHER PUBLICATIONS

Giles, Harold F. Jr. Extrusion—The Definitive Processing Guide and Handbook. © 2005 William Andrew Publishing.

United States Office Action dated Feb. 19, 2013, in U.S. Appl. No. 13/121,538.

* cited by examiner

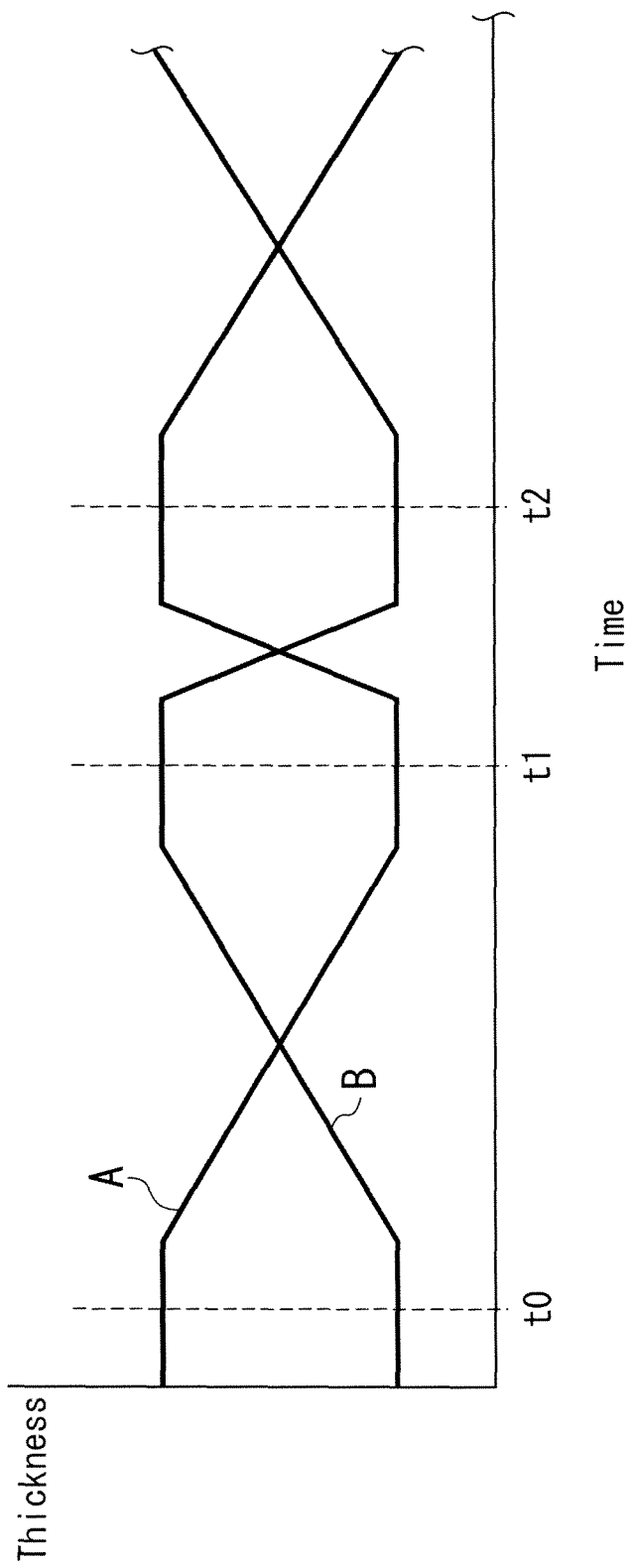

FIG.7

1. Thermoplastic polyurethane elastomer (TPU)
2. Thermoplastic polyester elastomer (TPEE)

| | Example1 | Example2 | Example3 | Comparative Example1 | Comparative Example2 | Comparative Example3 | Comparative Example4 | Comparative Example5 |
|---|---|---|---|---|---|---|---|---|
| Resin used | TPEE/TPU | TPEE/TPU | TPEE/TPU | TPU/TPU | TPEE/TPU | TPEE/TPU | TPEE/TPU | TPEE/TPU |
| Layer configuration | Laminate (upper layer/lower layer) TPEE/TPU | Laminate (upper layer/lower layer) TPEE/TPU | Laminate (upper layer/lower layer) TPEE/TPU | Laminate (upper layer/lower layer) TPU/TPU | Mixture | Laminate (upper layer/lower layer) TPEE/TPU | Laminate (upper layer/lower layer) TPEE/TPU | Laminate (upper layer/lower layer) TPEE/TPU |
| Thickness variation rate | 16 (8/2→2/8) | 6 (8/2→4/6) | 6 (8/2→4/6) | 16 (8/2→2/8) | — | 16 (8/2→2/8) | 16 (8/2→2/8) | 1 (5/5→5/5) |
| Melt viscosity ratio | 35 | 2 | 1 | 1 | 35 | 65 | 35 | 35 |
| Annealing | Applied | Applied | Applied | Applied | Applied | Applied | Not applied | Applied |
| Heat resistance/chemical resistance | G | G | G | P | P | G | G | G |
| Resilience/insertion performance | G | G | G | G | G | G | G | P |
| Variation of flexibility | G | G | G | G | G | P | G | G |
| Flexibility degradation | G | G | G | G | G | G | P | G | even
METHOD FOR PRODUCING ENDOSCOPE FLEXIBLE TUBE

BACKGROUND OF THE INVENTION

1. Field of the Invention

The present invention relates to a method for producing an endoscope flexible tube, in particular, a method for producing a flexible tube constituting the insertion portion of an endoscope.

2. Description of the Related Art

In general, an endoscope includes a proximal operating portion and an insertion portion connected in series to the proximal operating portion. The proximal operating portion is held by an operator and the insertion portion is inserted into the body of a subject.

The insertion portion is constituted with, sequentially from the proximal operating portion, a flexible tube portion, a bent portion and a distal end portion. The distal end portion is provided with an optical observation system including lenses and prisms. The flexible tube portion allows the passage therethrough of a forceps channel for guiding the passage of treatment tools, bent wires, a light guide, signal cables and the like.

The flexible tube as the main part constituting the insertion portion of an endoscope is constituted with a spiral tube formed by spirally winding a metal strip, a cylindrical mesh sleeve covering the spiral tube and an outer coat, made of urethane resin or the like, laminated on the surface of the cylindrical mesh sleeve. For the purpose of facilitating the insertion into the body, the distal end portion of the insertion portion is required to be high in flexibility and the flexible tube of the insertion portion is required to be low in flexibility and high in hardness in the side of the proximal operating portion. An endoscope is used repeatedly, and hence cleaned and sterilized. Therefore, the insertion portion is required to be heat resistant and chemical resistant.

Japanese Patent Application Laid-Open No. 2001-161632 discloses a case where the outer coat of the flexible tube includes as the main polymer thereof one or two of a thermoplastic polyurethane elastomer, a thermoplastic polyolefin elastomer and a thermoplastic polyester elastomer, for the purpose of enhancing the heat resistance and the chemical resistance of the insertion portion. However, when the main polymer includes only one material, there is a problem that the heat resistance, the chemical resistance and the operability are not satisfied simultaneously. On the other hand, when the outer coat is made of a mixture, there is a problem that the material low in heat resistance and chemical resistance may be located in the outside portion of the outer coat, and hence the insertion portion may be poor in heat resistance and chemical resistance.

Japanese Patent Application Laid-Open No. 2001-161633 discloses the constitution of the outer coat of the flexible tube with a mixed material composed of a thermoplastic polyurethane elastomer and a thermoplastic polyester elastomer, for the purpose of enhancing the heat resistance and the chemical resistance of the insertion portion. However, when the outer coat is formed of such a mixture, there is a problem that the material low in heat resistance and chemical resistance may be located in the outside portion of the outer coat, and hence the insertion portion may be poor in heat resistance and chemical resistance.

Japanese Patent Application Laid-Open No. 2001-333883 discloses a constitution of the outer coat with a laminate composed of an outer layer, an inner layer and an intermediate layer, and a partition of the intermediate layer into a plurality of regions through the intermediary of boundaries, for the purpose of enhancing the operability, the chemical resistance and the durability of the insertion portion. However, there is a problem that the lengthwise partition of the intermediate layer into the plurality of regions degrades the insertion performance.

Japanese Patent Application Laid-Open No. 2002-058637 discloses a lengthwise partition of the flexible tube into a plurality of regions and a weight reduction of the distal end portion as compared to the proximal portion. However, there is a problem that the lengthwise partition into the plurality of regions degrades the insertion performance.

Japanese Patent Application Laid-Open No. 2006-000281 discloses a control of the infiltration of an adhesive to the blade by specifying the annealing conditions or the aging conditions. However, there is a problem that the variation of the flexibility with time is large.

Japanese Utility Model Application Laid-Open No. 55-112505 discloses a flexible tube, provided with an outer coat, having a two layer structure composed of a soft resin layer and a hard resin layer wherein the proportion of the soft resin layer is increased in the side of the distal end of the flexible tube and the proportion of the hard resin layer is increased in the side of the proximal operating portion of the flexible tube. However, there is no specific disclosure of the fact that under what conditions a mesh-shaped tube is coated with the soft resin layer and the hard resin layer.

SUMMARY OF THE INVENTION

The present invention was achieved under such circumstances as described above, and an object of the present invention is to provide a method for producing an endoscope flexible tube excellent in operability, heat resistance and chemical resistance.

According to an embodiment of the present invention, provided is a method for producing an endoscope flexible tube including the steps of: preparing a flexible tube assembly including a spiral tube formed by spirally winding a metal strip and a cylindrical mesh sleeve, covering the spiral tube, formed by knitting metal wires; covering the flexible tube assembly with an outer coat from one end toward the other end of the flexible tube assembly by using an extrusion molding machine wherein the outer coat has a lower layer formed of a thermoplastic polyurethane elastomer and an upper layer formed of a thermoplastic polyester elastomer and the total thickness of the upper layer and the lower layer is made constant; and annealing the covered flexible tube assembly at a temperature in the vicinity of the softening point of the layer lower in softening point of the upper layer and the lower layer after the step of covering the flexible tube assembly with the outer coat; wherein in the step of covering with the outer coat, the melt viscosity ratio (thermoplastic polyurethane elastomer/thermoplastic polyester elastomer; with reference to the exit temperature of the extrusion molding machine) between the thermoplastic polyurethane elastomer and thermoplastic polyester elastomer is set to fall within a range from 1 to 35, and the thickness ratio between the upper layer and the lower layer is gradually varied in such a way that one of the upper layer and the lower layer has the maximum thickness at the one end and the one of the upper layer and the lower layer has the minimum thickness at the other end.

The disturbance of the interface between the lower layer and the upper layer can be prevented because the covering is performed with the thermoplastic polyurethane elastomer as the lower layer and the thermoplastic polyester elastomer as the upper layer, with the melt viscosity ratio of the thermoplastic polyurethane elastomer to the thermoplastic polyester elastomer being set to fall within a range from 1 to 35.

According to another embodiment of the present invention, preferably the production method satisfies the following formula:

$$6 \leq (A/B)/(C/D) \leq 16$$

wherein
- A: The thickness of the thicker layer at the one end
- B: The thickness of the thinner layer at the one end
- C: The thickness of the thinner layer at the other end
- D: The thickness of the thicker layer at the other end According to another embodiment of the present invention, the production method preferably further includes a step of cooling between the step of covering the flexible tube assembly with the outer coat and the step of annealing.

According to another embodiment of the present invention, the outer coat preferably has a region where the thickness ratio between the upper layer and the lower layer is constant in a predetermined length from the one end toward the other end and in a predetermined length from the other end toward the one end.

According to another embodiment of the present invention, preferably, the upper layer is thick and the lower layer is thin at the one end, and the upper layer is thin and the lower layer is thick at the other end.

According to another embodiment of the present invention, preferably, the upper layer is thin and the lower layer is thick at the one end, and the upper layer is thick and the lower layer is thin at the other end.

According to another embodiment of the present invention, preferably, the step of preparing the flexible tube assembly includes at least a step of connecting a plurality of the sets each composed of the flexible tube assembly and a dummy member in such a way that the flexible tube assemblies and the dummy members are alternately connected with a plurality of joint members.

According to the method for producing an endoscope flexible tube of the present invention, an endoscope flexible tube excellent in operability, heat resistance and chemical resistance can be produced.

BRIEF DESCRIPTION OF THE DRAWINGS

FIG. 6 is a graph showing the relation between the thickness of the upper layer and the time and the relation between the thickness of the lower layer and the time; and FIG. 7 is a table collecting the conditions and the evaluation results of Examples.

DETAILED DESCRIPTION OF THE PREFERRED EMBODIMENTS

Hereinafter, the preferred embodiments of the present invention are described with reference to the accompanying drawings. Although hereinafter the present invention is described on the basis of the preferred embodiments, the present invention may be modified by many manners without deviating from the scope of the present invention, and embodiments other than the present embodiments may be utilized. Therefore, all the modifications falling within the scope of the present invention are included in what is claimed. In the present specification, a numerical value range indicated with "to" means the range inclusive of the numerical values described before and after "to."

Figure 1:
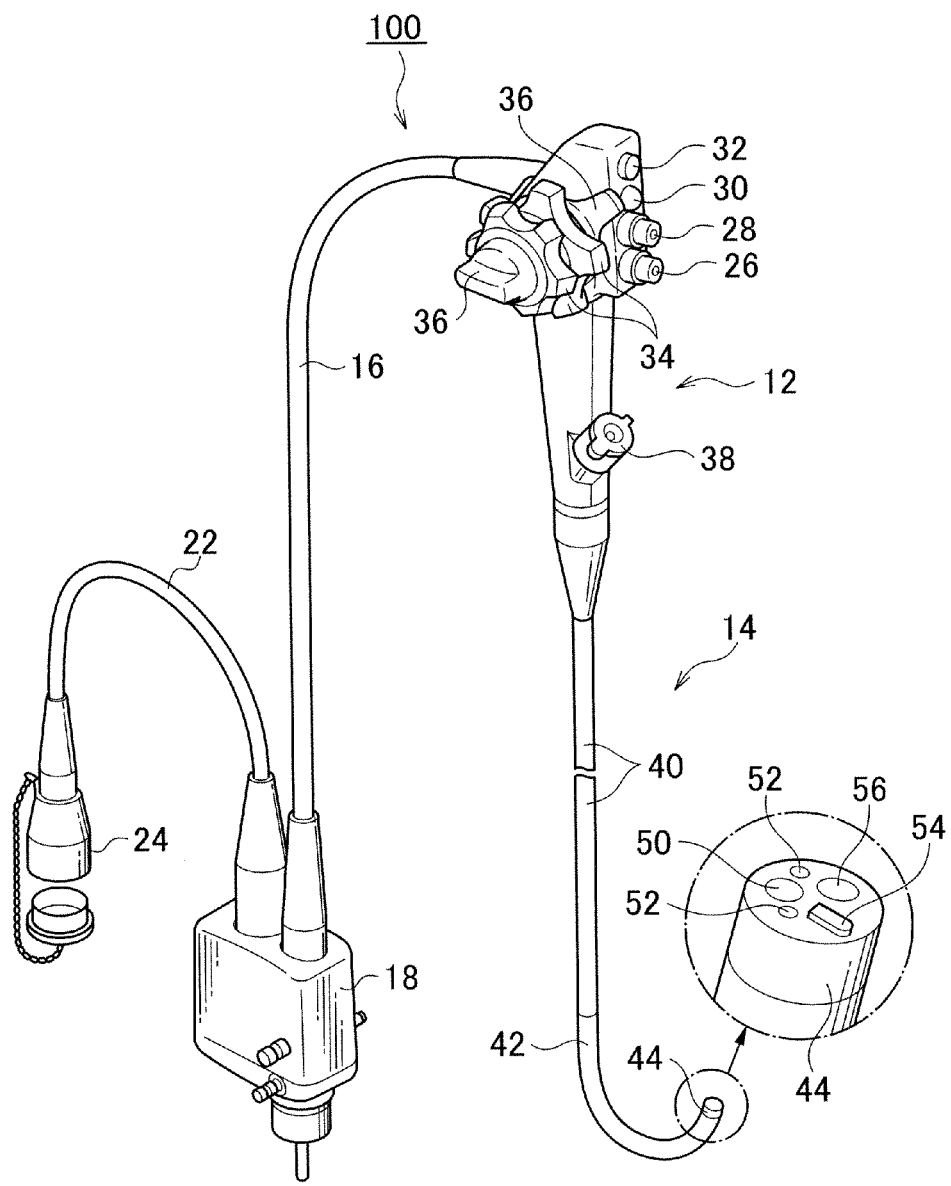
FIG. 1 is an oblique perspective view illustrating an endoscope.

FIG. 1 is an oblique perspective view illustrating an endoscope. As shown in FIG. 1, the endoscope 100 includes a proximal operating portion 12 and an insertion portion 14 connected in series to the proximal operating portion 12. The proximal operating portion 12 is held by an operator and the insertion portion 14 is inserted into the body of a subject.

A universal cable 16 is connected to the proximal operating portion 12, and an LG connector 18 is provided at the distal end of the universal cable 16. By connecting the LG connector 18 to a not-shown light source device in a freely attachable and detachable manner, illuminating light is transmitted to an illuminating optical system 52 provided at the distal end portion of the insertion portion 14. To the LG connector 18, an electric connector 24 is connected through the intermediary of a cable 22, and the electric connector 24 is connected to a not-shown processor in a freely attachable and detachable manner. Thus, the observed image data obtained in the endoscope 100 is output to the processor, and further the image is displayed on a monitor (not shown) connected to the processor.

In the proximal operating portion 12, an air feed/water feed button 26, a suction button 28, a shutter button 30 and a function change-over button 32 are provided close each other in a row. The air feed/water feed button 26 is an operating button for jetting air or water toward an observation optical system 50 from an air feed/water feed nozzle 54 provided at the distal end portion 44 of the insertion portion 14, and the suction button 28 is an operating button for sucking a lesion portion or the like from a forceps opening 56 provided at the distal end portion 44. The shutter button 30 is an operating button for operating the recording and the like of the observed image, and the function change-over button 32 is an operating button for changing over the functions such as the functions of the shutter button 30.

Additionally, in the proximal operating portion 12, a pair of angular knobs 34 and 34 and a pair of lock levers 36 and 36 are provided; by operating the angular knobs 34, the below-described bent portion 42 is made to undergo bending operation, and by operating the lock levers 36, the angular knobs 34 are made to be fixed or to be released from fixation.

Further, in the proximal operating portion 12, a forceps insertion portion 38 is provided, and the forceps insertion portion 38 is communicatively connected to the forceps opening 56 at the distal end portion 44. Therefore, by inserting the endoscope treatment tools (not shown) such as a pair of forceps from the forceps insertion portion 38, the endoscope treatment tools can be lead out from the forceps opening 56.

On the other hand, the insertion portion 14 is constituted with, sequentially from side of the proximal operating portion 12, a flexible tube 40, the bent portion 42 and the distal end portion 44.

Figure 2:
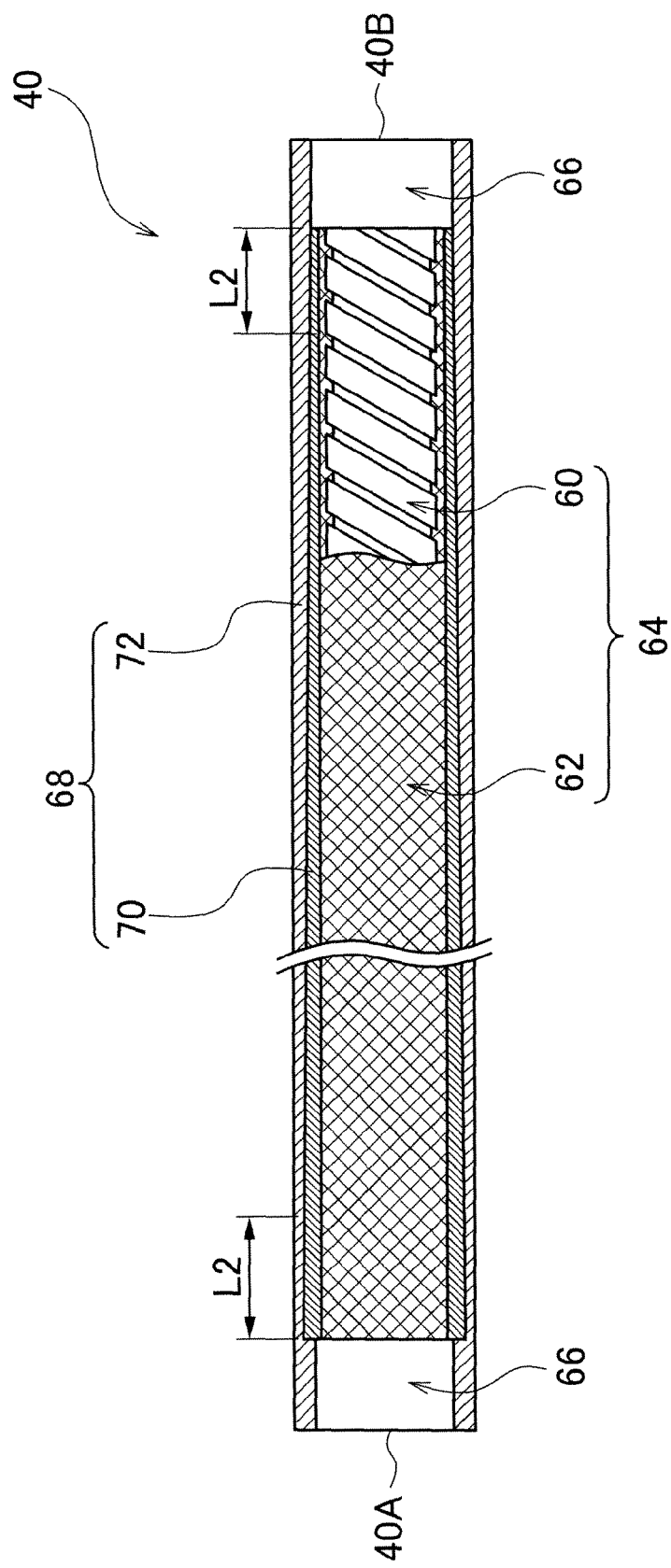
FIG. 2 is a partial cross sectional view illustrating the structure of an endoscope flexible tube.

FIG. 2 is an enlarged partial cross sectional view of the flexible tube constituting the endoscope flexible tube. The flexible tube 40 includes a flexible tube assembly 64 constituted with a spiral tube 60, as the innermost member, formed by spirally winding a metal strip and a cylindrical mesh sleeve 62, covering the spiral tube 60, formed by knitting metal wires. A ferrule 66 is provided at each of both ends of the flexible tube assembly 64. The cylindrical mesh sleeve 62 is covered with an outer coat 68. Further, the outer coat 68 is covered with a chemical-resistant coating film (not shown) containing, for example, silicon.

The outer coat 68 includes two layers, namely, a lower layer 70 of a thermoplastic polyurethane elastomer and an upper layer 72 of a thermoplastic polyester elastomer. The outer coat 68 is formed in such a way that the total thickness of the lower layer 70 and the upper layer 72 is approximately constant. The lower layer 70 of a thermoplastic polyurethane elastomer has softness and the upper layer 72 of a thermoplastic polyester elastomer has hardness. The thermoplastic polyurethane elastomer as referred to herein is defined as a rubbery elastic body obtained by the reaction of polyester or polyether with isocyanate, as shown in the following structural formulas.

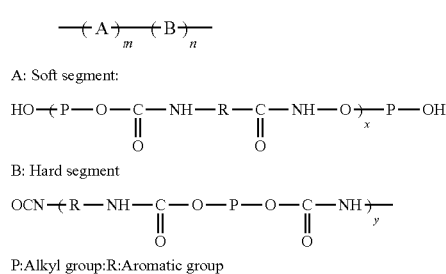

[Formula 1]

The thermoplastic polyester elastomer as referred to herein is defined as a thermoplastic elastomer which can be produced by using as the raw materials dimethyl terephthalate, 1,4-butanediol and poly(oxytetramethylene) glycol and by applying transesterification reaction or polycondensation reaction, as shown in the following structural formula.

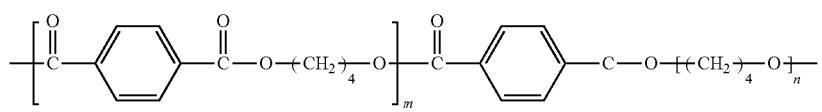

[Formula 2]

In FIG. 2, the left side of the flexible tube 40 is the side of a distal end 40A and the right side of the flexible tube 40 is the side of the proximal operating portion, namely, the side of a proximal end 40B. The lower layer 70 has the maximum thickness on the side of the distal end 40A, and is gradually decreased in thickness from the side of the distal end 40A toward the side of the proximal end 40B and has the minimum thickness on the side of the proximal end 40B. On the other hand, the upper layer 72 has the minimum thickness on the side of the distal end 40A, and is gradually increased in thickness from the side of the distal end 40A toward the side of the proximal end 40B and has the maximum thickness on the side of the proximal end 40B. The lower layer 70 and the upper layer 72 are formed in such a way that the total thickness of the lower layer 70 and the upper layer 72 is approximately constant, and hence as shown in FIG. 2, the thickness ratio of the lower layer 70 and the upper layer 72 is gradually varied from the side of the distal end 40A toward the proximal end 40B. With this structure, the flexible tube 40 exhibits the properties such that the softness is high on the side of the distal end 40A and the softness is low and the hardness is high on the side of the proximal end 40B. In an actual endoscope, the bent portion is connected on the side of the distal end 40A of the flexible tube 40 and the proximal operating portion is connected on the side of the proximal end 40B of the flexible tube 40.

As shown in FIG. 2, in the flexible tube 40, the thickness ratio between the lower layer 70 and the upper layer 72 is constant in the predetermined length L1 from the distal end 40A toward the proximal end 40B and in the predetermined length L2 from the proximal end 40B toward the distal end 40A.

Figure 3:
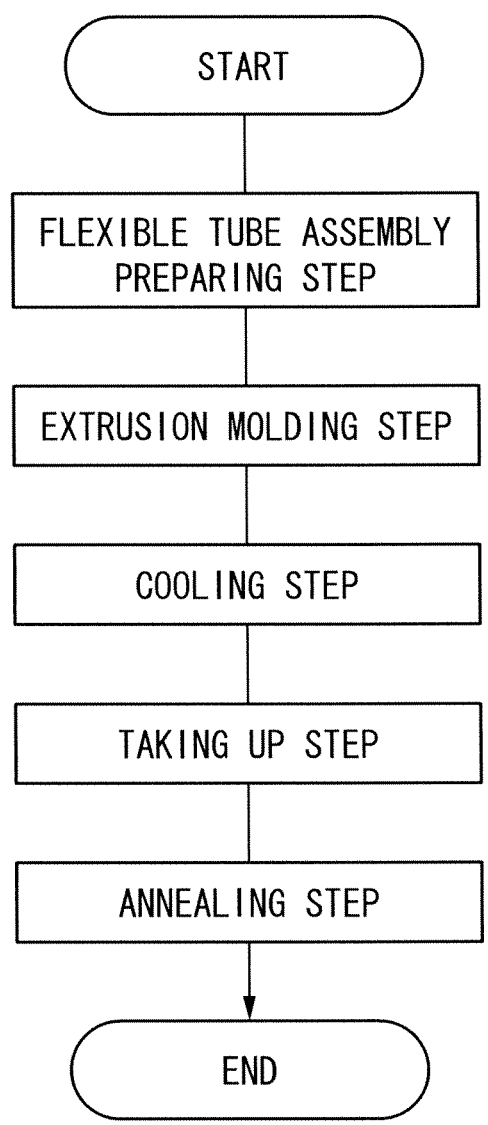
FIG. 3 is a flow chart illustrating a method for producing the endoscope flexible tube.

Next, the method for producing the endoscope flexible tube of the present embodiment is described. FIG. 3 shows the flow of the method for producing the endoscope flexible tube. First, the step of preparing the flexible tube assembly prepares the flexible tube assembly formed by covering the spiral tube with the cylindrical mesh sleeve. In this case, a plurality of flexible tube assemblies and a plurality of dummy members are alternately connected with joint members. Next, the connected plurality of the flexible tube assemblies is transferred to an extrusion molding machine. In the step of extrusion molding, an extrusion molding machine covers the surface of the flexible tube assemblies with the outer coat having a two layer structure constituted with the lower layer of a thermoplastic polyurethane elastomer and the upper layer of a thermoplastic polyester elastomer. The covering is performed in such a way that the total thickness of the upper layer and the lower layer is set to be constant and the thickness ratio is gradually varied from one end toward the other end. In the cooling step, the flexible tube assemblies covered with the outer coat is cooled, for example, with water. In the taking-up step, the flexible tube assemblies covered with the outer coat is wound up on a drum. Subsequently, the joint members and the dummy members of the plurality of the connected flexible tube assemblies covered with the outer coat are removed. The flexible tube assemblies covered with the outer coat are separated into individual flexible tube assemblies. In the annealing step, the flexible tube assemblies covered with the outer coat is allowed to stand in an atmosphere at a temperature in the vicinity of the softening point of the thermoplastic polyurethane elastomer for a predetermined time to be subjected to a heat treatment.

Figure 4:
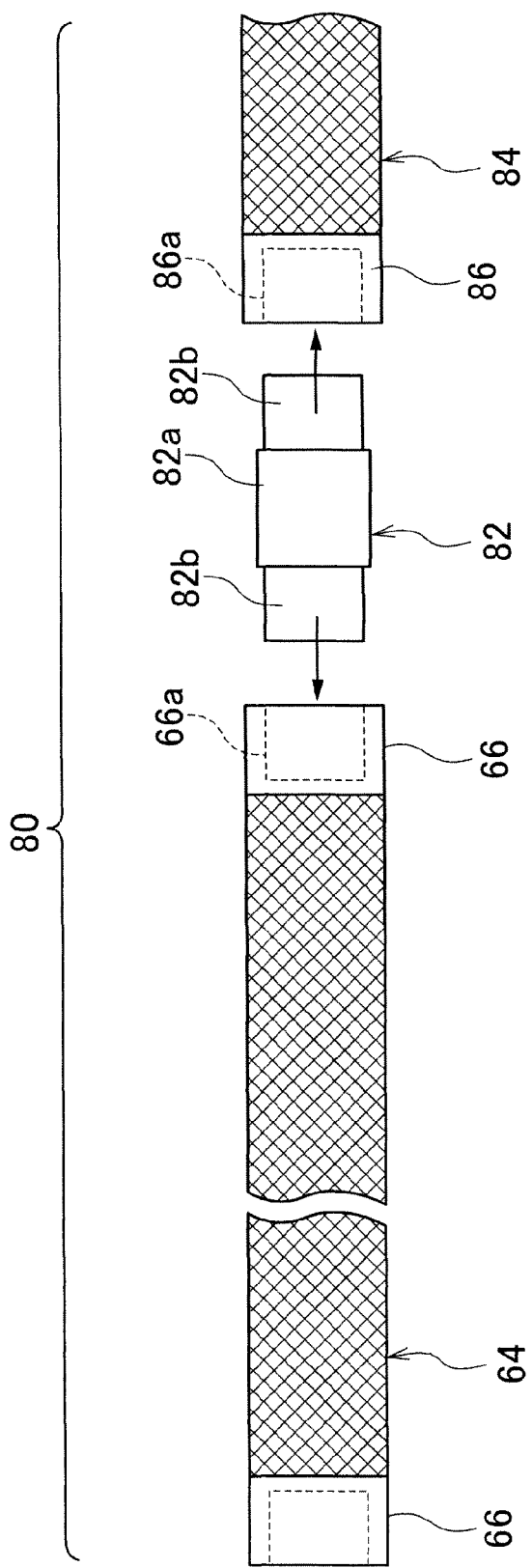
FIG. 4 is a schematic view illustrating a structure in which a plurality of flexible tube assemblies are connected with joint members.

Next, the method for producing the endoscope flexible tube is specifically described. FIG. 4 shows the step of preparing the flexible tube assemblies. As shown in FIG. 4, by connecting a plurality of the flexible tube assemblies 64, a set of the connected flexible tube assemblies 80 constituted as a string of wire is prepared. The plurality of the flexible tube assemblies 64 are connected to the dummy members 84 through the intermediary of the joint members 82. The joint members 82 each includes the main body 82a and the joints 82b disposed on both sides of the main body 82a. One of the joints 82b is inserted into the inner circumference 66a (indicated with a dotted line) of the ferrule 66 disposed at the end of the flexible tube assembly 64. The other joint 82b of the joint member 82 is inserted into the inner circumference 86a (indicated with a dotted line) of the ferrule 86 at one end of the dummy member 84. The set of the connected flexible tube assemblies 80 is assembled by sequentially repeating the connection of the flexible tube assembly 64, the joint member 82, the dummy member 84 and the joint member 82.

Figure 5:
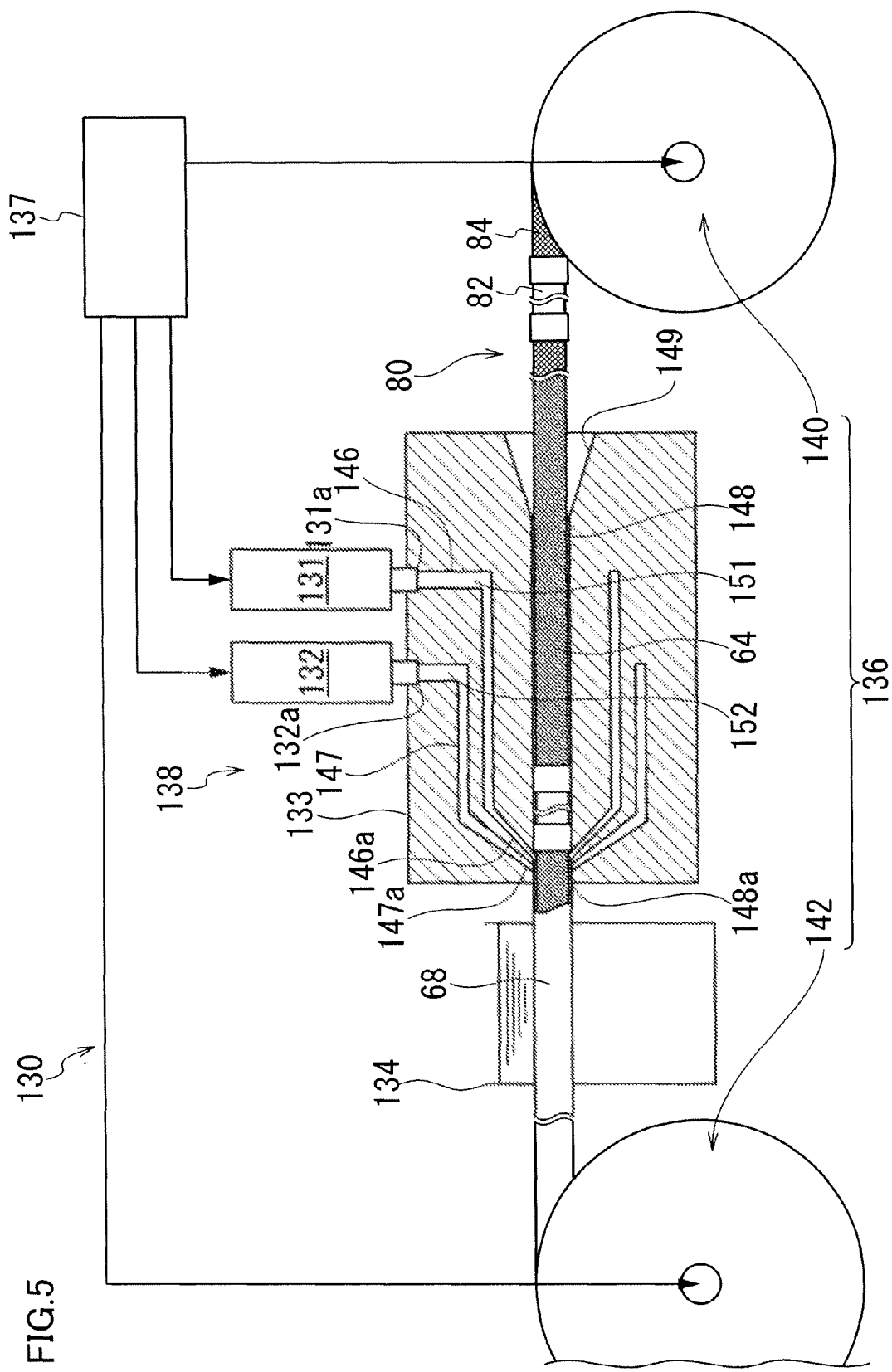
FIG. 5 is a schematic view illustrating a schematic configuration of a continuous molding facility.

Next, with reference to the continuous molding facility shown in FIG. 5, the extrusion molding step, the cooling step and the taking-up step are described. The continuous molding facility 130 includes extrusion sections 131 and 132 each equipped with a hopper, a screw and the like, a head section 133 for molding the outer coat on the outer circumferential surface of the connected flexible tube assemblies 80, a cooling section 134, a conveying section 136 for conveying the connected flexible tube assemblies 80 to the head section 133 and a controlling section 137 for controlling these sections. The head section 133 and the extrusion sections 131 and 132 constitute the extrusion molding machine 138.

The conveying section 136 is constituted with a feeding drum 140 and a winding-up drum 142. The connected flexible tube assemblies 80 are rolled up on the feeding drum 140, then sequentially taken out, made to pass through the extrusion molding machine 138 for molding the outer coat 68 and the cooling section 134 for cooling the outer coat 68 after molding, and wound up on the winding-up drum 142. The feeding drum 140 and the winding-up drum 142 are controlled in rotation by the controlling section 137 to change over the conveying speed for conveying the connected flexible tube assemblies 80.

In the extrusion sections 131 and 132, discharge openings 131a and 132a are respectively connected to gates 146 and 147 of the head section 133. From the extrusion section 131, the thermoplastic polyurethane elastomer 151 in a molten state is fed to the gate 146, and from the extrusion section 132, the thermoplastic polyester elastomer 152 in a molten state is fed to the gate 147. The extrusion sections 131 and 132 are controlled in extrusion pressure by the controlling section 137. The control of the extrusion pressures (the rotation speeds of the screws) of the extrusion sections 131 and 132 enables to regulate the molding thicknesses of the lower layer and the upper layer covering the flexible tube assembly 64.

The head section 133 has a circular hole 148 formed therein to determine the outer circumferential shape of the outer coat molded on the outer circumference of the connected flexible tube assemblies 80, and the feed ports 146a and 147a of the gates 146 and 147 are connected to the circular hole 148. The head section 133 is provided with a conical recessed portion 149, which is connected to the circular hole 148, for guiding the insertion of the connected flexible tube assemblies 80.

The feed ports 146a and 147a of the gates 146 and 147 are located in the vicinity of the exit 148a of the circular hole 148, and the feed port 146a is located upstream and the feed port 147a is located downstream. Thus, the thermoplastic polyurethane elastomer 151 in a molten state, fed from the gate 146, is laminated on the connected flexible tube assemblies 80, in advance of the thermoplastic polyester elastomer 152 in a molten state fed from the gate 147. The soft thermoplastic polyurethane elastomer 151 is formed as the lower layer and the hard thermoplastic polyester elastomer 152 is formed as the upper layer.

In the present embodiment, the ratio (thermoplastic polyurethane elastomer/thermoplastic polyester elastomer: exit temperature; with reference to the exit temperature of the extrusion molding machine) between the melt viscosity of the thermoplastic polyurethane elastomer 151 discharged from the feed port 146a and the melt viscosity of the thermoplastic polyester elastomer 152 discharged from the feed port 147a, namely, the so-called melt viscosity ratio is set to fall within a range from 1 to 35. The formation of the outer coat 68 on the flexible tube assembly 64, within the melt viscosity ratio, with the thermoplastic polyurethane elastomer 151 as the lower layer and the thermoplastic polyester elastomer 152 as the upper layer enables to prevent the disturbance of the interface between the upper layer and the lower layer, and enables to cover the flexible tube assembly with the upper layer and the lower layer each having a predetermined thickness.

The exit 148a of the circular hole 148 in the head section 133 is formed in such a way that the inner diameter of the exit 148a fits the outer diameter of the outer coat 68 formed on the outer circumference of the flexible tube assembly 64. Immediately after the lamination of the thermoplastic polyurethane elastomer 151 and the thermoplastic polyester elastomer 152 respectively discharged from the gates 146 and 147, the connected flexible tube assemblies 80 pass through the exit 148a and hence the outer coat 68 is formed so as to have a uniform outer diameter.

The covering of the flexible tube assembly 64 with the outer coat 68 may adopt either of the following two patterns (1) and (2): (1) a pattern in which thermoplastic polyurethane elastomer 151 as the lower layer is formed thin, the thermoplastic polyester elastomer 152 as the upper layer is formed thick, and the ratio between the lower layer and the upper layer is gradually varied in such a way that the thermoplastic polyurethane elastomer 151 as the lower layer is formed thick and the thermoplastic polyester elastomer 152 as the upper layer is formed thin; (2) a pattern in which the thermoplastic polyurethane elastomer 151 as the lower layer is formed thick, the thermoplastic polyester elastomer 152 as the upper layer is formed thin, and the ratio between the lower layer and the upper layer is gradually varied in such a way that the thermoplastic polyurethane elastomer 151 as the lower layer is formed thin and the thermoplastic polyester elastomer 152 as the upper layer is formed thick.

On completion of the covering of the flexible tube assembly 64 with the outer coat 68, the joint member 82 and the dummy member 84 are conveyed to the head section 133. The dummy member 84 is also covered with the outer coat 68 in the same manner in such a way that lower layer is formed of the thermoplastic polyurethane elastomer 151 and the upper layer is formed of the thermoplastic polyester elastomer 152. In this case, the ratio between the lower layer and the upper layer formed on the dummy member 84 is the same as the ratio between the lower layer and the upper layer in the state of completion of the covering of the flexible tube assembly 64 with the outer coat 68. Subsequently, the ratio between the lower layer and the upper layer formed on the dummy member 84 is gradually varied so as to be the same as the ratio between the lower layer and the upper layer in the state of starting the covering of the flexible tube assembly 64 with the outer coat 68. Then, the covering of the flexible tube assembly 64 with the outer coat 68 is started.

In the present embodiment, for the covering of the flexible tube assembly with the outer coat, the above-described pattern (1) or (2) is repeatedly performed.

The connected flexible tube assemblies 80 with the outer coat 68 molded thereon passes through the head section 133 and then passes through the cooling section 134. In the cooling section 134, a cooling liquid such as water is reserved. The connected flexible tube assemblies 80 with the outer coat 68 molded thereon are made pass through the cooling liquid. The reasons for making the connected flexible tube assemblies 80 pass through the cooling liquid are as follows.

The temperature of the exit 148a of the die is extremely high and the outer coat 68 covering the connected flexible tube assemblies 80, namely, the resin is in a state capable of being fluidized. If the passing through the cooling liquid is not performed and the connected flexible tube assemblies 80 are allowed to stand at such high temperatures, the resin is fluidized and the connected flexible tube assemblies 80 are decentered. In other words, the resin sags due to its own weight, and thus the resin thickness comes to have a distribution in the circumferential direction. Thus, the reasons are ascribable to the fact that such decentering results in a circumferential distribution of the bending hardness of the flexible tube and the operability is degraded. By making the connected flexible tube assemblies 80 pass through the cooling liquid, the fluidity of the outer coat 68, namely, the fluidity of the resin can be suppressed. Instead of this way, the outer coat 68 may be cooled by blowing the cooling liquid or air to the outer coat 68. The connected flexible tube assemblies 80 having been made to pass through the cooling section 134 are taken up on the winding-up drum 142.

In the annealing step, the joint members and the dummy members of the connected flexible tube assemblies 80 are disconnected to lead to a condition of being the flexible tube assembly 64 covered with the outer coat 68. The flexible tube assembly 64 is heat treated by being allowed to stand for about 1 hour in the atmosphere set at a temperature in the vicinity of the softening point of the thermoplastic polyurethane elastomer of the lower layer. The reasons for performing the annealing step are as follows.

The molded outer coat 68, namely, the resin is not yet in an ordered condition at a molecular level. Therefore, the outer coat 68 is still in a condition of being movable. When the outer coat 68 is exposed to a low temperature for a while, the molecular structure thereof is stabilized, and thus the degradation of the flexibility is made small. In other words, the annealing enables the molecular structure of the resin constituting the outer coat 68 to be stabilized.

FIG. 6 is a graph conceptually showing the relation between the thicknesses of the lower layer and the upper layer formed on the connected flexible tube assemblies and the time. The graph A represents the thickness of the thermoplastic polyester elastomer as the upper layer and the graph B represents the thickness of the thermoplastic polyurethane elastomer as the lower layer. The time t0 indicates the time at which the covering of the flexible tube assembly with the outer coat is started. The time t1 indicates the time at which the covering of the flexible tube assembly with the outer coat is completed and the covering of the dummy member with the outer coat is started. The time t2 indicates the time at which the covering of the dummy member with the outer coat is completed and the covering of the next flexible tube assembly with the outer coat is started. FIG. 6 represents the case where the covering of the outer coat is performed according to the above-described pattern (1).

As shown in FIG. 6, the covering with the outer coat is started at t0. The thermoplastic polyurethane elastomer as the lower layer is formed thin, and the thermoplastic polyester elastomer as the upper layer is formed thick. Next, for a predetermined period of time, the covering with the outer coat is performed under the condition that the thicknesses of the lower layer and the upper layer are not varied. Next, the lower layer is formed to be gradually thick and the upper layer is formed to be gradually thin. The outer coat is formed until the thickness order of the lower layer and the upper layer is reversed, the lower layer attains a predetermined thickness and the upper layer attains a predetermined thinness. Next, for a predetermined period of time, the covering with the outer coat is performed under the condition that the thicknesses of the lower layer and the upper layer are not varied. At t1, the covering of the flexible tube assembly with the outer coat is completed. Next, the covering of the dummy member with the outer coat is started. The lower layer is formed to be gradually thin and the upper layer is formed to be gradually thick. The lower layer is formed thin and the upper layer is formed thick until the thickness order of the lower layer and the upper layer is reversed and the thicknesses of the lower layer and the upper layer are the same as these thicknesses at t0. Next, at t2, the covering of the dummy member with the outer coat is completed. Then, the covering of the next flexible tube assembly with the outer coat is started. During the covering with the outer coat, the lower layer and the upper layer are formed with the melt viscosity ratio falling within the range from 1 to 35.

EXAMPLES

Hereinafter, the present invention is more specifically described with reference to Examples. The materials, the amounts of the materials used, the proportions of the materials, the treatment details, the treatment procedures and the like shown in following Examples may be optionally modified as long as such modifications do not deviate from the gist of the present invention. Accordingly, the scope of the present invention is not limited by the following specific examples.

By using the continuous molding facility shown in FIG. 5, a flexible tube assembly was covered with an outer coat composed of thermoplastic polyurethane elastomer as the lower layer and thermoplastic polyester elastomer as the upper layer. The rotation numbers of the screws of two extruders (extrusion section) were respectively continuously varied, resins were respectively discharged within a temperature range from 190° C. to 210° C. In this way, the thickness ratio between the lower layer and the upper layer was varied.

The melt viscosity ratio was measured with a flow tester. The measured values at the exit temperature of the feed port of the head section were used. An annealing treatment was performed by allowing the flexible tube assembly covered with an outer coat to stand for 1 hour in an atmosphere set at a temperature in the vicinity of the softening point (110° C.) of the resin (thermoplastic polyurethane elastomer) having the lowest softening point.

For evaluating the heat resistance, a sheet-shaped specimen prepared by using the constituent materials of the endoscope outer coat (thickness: 0.5 mm, length: 50 mm, width: 10 mm) was subjected to repeated cycles of heating and cooling, and thus the degradation of the flexibility was tested. Specifically, the following set of operations was repeated ten times for each specimen: the specimen was treated in an autoclave under a pressure of 2 atm at 135° C. for 20 minutes, and then rapidly cooled with ice water.

For evaluating the chemical resistance, a sheet-shaped specimen prepared by using the constituent materials of the endoscope outer coat (thickness: 0.5 mm, length: 50 mm, width: 10 mm) was immersed in dimethylformamide (DMF) for 1 week, and the volume difference of the specimen between before and after the immersion was evaluated. The evaluation was performed on the basis of the following standards: G (good): insoluble in DMF; A (average): 10% by volume or less of swelling; P (poor): 10% by volume or more of swelling or soluble in DMF.

The resilience and the insertion performance were evaluated by bending the endoscope flexible tube. The cases of being rich, scarce and almost null in resilience were marked with G (good), A (average) and P (poor), respectively.

The resilience as referred to herein means the time variation (after the elapsed time of 10 seconds) of the reaction force exerting when the flexible tube is bent to a predetermined distance. The conditions of being rich, scarce and almost null in resilience correspond to the variation rates (degradation rates) of the reaction force of 30% or less, 30 to 70%, and 70% or more, respectively.

For evaluating the flexibility, the bending operation of the endoscope flexible tube was repeated for 3 minutes, and the degradation of the flexibility was tested. The reaction force values for the bending of flexible tube specimens in a predetermined distance were measured with a force gauge, and the differences between the individual specimens were compared. The case where the differences between the individual specimens (10 specimens) were 10% or more was marked with P (poor), and the case where the differences between the individual specimens (10 specimens) were less than 10% was marked with G (good).

In Example 1, a thermoplastic polyurethane elastomer and a thermoplastic polyester elastomer were adopted for the lower layer and the upper layer, respectively, and the thickness variation rate derived from the following formula was set at 16.

$$\text{Thickness variation rate} = (A/B)/(C/D)$$

wherein A denotes the thickness of the thicker layer at the one end, B denotes the thickness of the thinner layer at the one end, C denotes the thickness of the thinner layer at the other end, and D denotes the thickness of the thicker layer at the other end.

When the covering with the outer coat was performed, the melt viscosity ratio (thermoplastic polyurethane elastomer/thermoplastic polyester elastomer) was set at 35. After the covering with the outer coat, an annealing treatment was performed.

Example 2 was the same manner as Example 1 except that the thickness variation rate was set at 6 and the melt viscosity ratio was set at 2.

Example 3 was the same manner as Example 1 except that the thickness variation rate was set at 6 and the melt viscosity ratio was set at 1.

Comparative Example 1 adopted an outer coat layer configuration composed of two layers of a thermoplastic polyurethane elastomer. In this case, the melt viscosity ratio was 1. Otherwise, Comparative Example 1 was the same as Example 1.

Comparative Example 2 adopted an outer coat layer configuration composed of a mixed layer of a thermoplastic polyurethane elastomer and a thermoplastic polyester elastomer.

Comparative Example 3 was the same as Example 1 except that the melt viscosity ratio was set at 65.

Comparative Example 4 was the same as Example 1 except that no annealing treatment was performed. Comparative Example 5 was the same as Example 1 except that the thickness variation rate was set at 1. The thickness variation rate of 1 means that both of the lower layer and the upper layer do not vary in layer thickness from one end toward the other end.

Table 1 shown in FIG. 7 collects the conditions and the evaluation results of Examples 1 to 3 and Comparative Examples 1 to 5.

In each of Examples 1 to 3, the melt viscosity ratio fell within the range from 1 to 35. Consequently, Examples 1 to 3 were each evaluated to be marked with G (good) with respect to the heat resistance/chemical resistance, the resilience/insertion performance, the flexibility variation and the flexibility required for the endoscope flexible tube.

Comparative Example 1 adopted a thermoplastic polyurethane elastomer poor in heat resistance and chemical resistance, and hence the heat resistance and the chemical resistance were evaluated to be marked with P (poor).

Comparative Example 2 adopted an outer coat composed of a mixed layer, and hence the heat resistance and the chemical resistance were evaluated to be marked with P (poor) as compared to Examples 1 to 3 in each of which the upper layer was a single layer of a thermoplastic polyester elastomer.

Comparative Example 3 adopted a viscosity ratio exceeding 35, and hence had a large variation of flexibility between the individual specimens and was evaluated to be marked with P (poor). Comparative Example 4 did not adopt the annealing, and hence the degradation of the flexibility with time was evaluated to be marked with P (poor). Comparative Example 5 was free from the variation of the thickness ratio, and hence the operability and the resilience were evaluated to be marked with P (poor).

What is claimed is:

1. A method for producing an endoscope flexible tube, said method comprising:
preparing a flexible tube assembly including a spiral tube formed by spirally winding a metal strip and a cylindrical mesh sleeve, covering the spiral tube, formed by knitting metal wires;
covering the flexible tube assembly with an outer coat from one end toward another end of the flexible tube assembly by using an extrusion molding machine, wherein the outer coat comprises a lower layer comprising a thermoplastic polyurethane elastomer and an upper layer comprising a thermoplastic polyester elastomer, and a total thickness of the upper layer and the lower layer is constant; and
annealing the covered flexible tube assembly at a temperature in a vicinity of a softening point of a layer with a lower softening point out of the upper layer and the lower layer after the covering the flexible tube assembly with the outer coat,
wherein in the covering with the outer coat, a melt viscosity ratio, as thermoplastic polyurethane elastomer/thermoplastic polyester elastomer, with reference to an exit temperature of the extrusion molding machine, between the thermoplastic polyurethane elastomer and the thermoplastic polyester elastomer is set to fall within a range from 1 to 35, and a thickness ratio between the upper layer and the lower layer is gradually varied in such a way that one of the upper layer and the lower layer has a maximum thickness at the one end and the one of the upper layer and the lower layer has a minimum thickness at the another end, and
wherein the preparing the flexible tube assembly comprises at least connecting a plurality of sets each comprising the flexible tube assembly and a dummy member in such a way that the flexible tube assemblies and the dummy members are alternately connected with a plurality of joint members.

2. The method for producing an endoscope flexible tube according to claim 1, wherein the method satisfies the following formula:

$$6 \leq (A/B)/(C/D) \leq 16$$

wherein
A: A thickness of a thicker layer at the one end
B: A thickness of a thinner layer at the one end
C: The thickness of the thinner layer at the another end
D: The thickness of the thicker layer at the another end.

3. The method for producing an endoscope flexible tube according to claim 1, further comprising cooling between the covering the flexible tube assembly with the outer coat and the annealing.

4. The method for producing an endoscope flexible tube according to claim 1, wherein the outer coat comprises a region where the thickness ratio between the upper layer and the lower layer is constant at a predetermined length from the one end toward the another end and at a predetermined length from the another end toward the one end.

5. The method for producing an endoscope flexible tube according to claim 1, wherein the upper layer is thick and the lower layer is thin at the one end, and the upper layer is thin and the lower layer is thick at the another end.

6. The method for producing an endoscope flexible tube according to claim 1, wherein the upper layer is thin and the lower layer is thick at the one end, and the upper layer is thick and the lower layer is thin at the another end.

7. The method for producing an endoscope flexible tube according to claim 1, wherein the covering with the outer coat includes coating the dummy member in a manner that a thickness order of the lower layer and the upper layer is reversed from the one end toward the another end while the total thickness of the lower layer and the upper layer is kept constant.

8. The method for producing an endoscope flexible tube according to claim 1, wherein each of the joint members comprises:
  a main body; and
  a first joint and a second joint disposed on opposing sides of the main body.

9. The method for producing an endoscope flexible tube according to claim 8, wherein, in each of said sets, the first joint is inserted into an inner circumference of a ferrule disposed at one of the one end and the another end of the flexible tube assembly, and the second joint is inserted into an inner circumference of a ferrule disposed at an end of the dummy member.

10. The method for producing an endoscope flexible tube according to claim 1, wherein a thickness of the upper layer continuously decreases from the one end to the another end of the flexible tube assembly.

* * * * *